US009522965B2

(12) United States Patent
Chen et al.

(10) Patent No.: US 9,522,965 B2
(45) Date of Patent: Dec. 20, 2016

(54) SEQUENTIAL HYDROTHERMAL LIQUIFACTION (SEQHTL) FOR EXTRACTION OF SUPERIOR BIO-OIL AND OTHER ORGANIC COMPOUNDS FROM OLEAGINOUS BIOMASS

(71) Applicant: Washington State University, Pullman, WA (US)

(72) Inventors: Shulin Chen, Pullman, WA (US); Moumita Chakraborty, Pullman, WA (US); Chao Miao, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 14/353,823

(22) PCT Filed: Oct. 24, 2012

(86) PCT No.: PCT/US2012/061648
§ 371 (c)(1),
(2) Date: Apr. 24, 2014

(87) PCT Pub. No.: WO2013/063085
PCT Pub. Date: May 2, 2013

(65) Prior Publication Data
US 2014/0296495 A1    Oct. 2, 2014

Related U.S. Application Data

(60) Provisional application No. 61/550,800, filed on Oct. 24, 2011.

(51) Int. Cl.

| | |
|---|---|
| *A01N 65/00* | (2009.01) |
| *A61K 36/02* | (2006.01) |
| *A61K 36/00* | (2006.01) |
| *C07K 1/00* | (2006.01) |
| *C07K 14/00* | (2006.01) |
| *C07K 14/37* | (2006.01) |
| *C07K 16/00* | (2006.01) |
| *C07K 17/00* | (2006.01) |
| *C12N 1/12* | (2006.01) |
| *C12N 1/00* | (2006.01) |
| *C08B 37/00* | (2006.01) |
| *C10L 1/02* | (2006.01) |
| *B01J 6/00* | (2006.01) |
| *C07K 1/14* | (2006.01) |
| *C11C 1/00* | (2006.01) |
| *C11B 1/10* | (2006.01) |
| *A61K 36/05* | (2006.01) |
| *C12N 1/20* | (2006.01) |
| *A61K 8/97* | (2006.01) |
| *C07K 14/415* | (2006.01) |
| *A01G 33/00* | (2006.01) |

(52) U.S. Cl.
CPC .............. *C08B 37/0003* (2013.01); *B01J 6/00* (2013.01); *C07K 1/145* (2013.01); *C10L 1/02* (2013.01); *C11B 1/10* (2013.01); *C11C 1/007* (2013.01); *A01G 33/00* (2013.01); *A61K 8/975* (2013.01); *A61K 36/05* (2013.01); *C07K 14/415* (2013.01); *C12N 1/12* (2013.01); *C12N 1/20* (2013.01); *Y02P 30/20* (2015.11)

(58) Field of Classification Search
CPC ...... A61K 8/975; A61K 36/05; C07K 14/415; C12N 1/12; C12N 1/20; A01G 33/00
See application file for complete search history.

(56) References Cited

U.S. PATENT DOCUMENTS

| | | | | |
|---|---|---|---|---|
| 8,920,609 | B2 * | 12/2014 | Steele et al. | 203/87 |
| 9,028,696 | B2 * | 5/2015 | Cranford | C11B 1/02 210/639 |
| 2010/0050502 | A1 | 3/2010 | Wu et al. | |
| 2010/0233761 | A1 * | 9/2010 | Czartoski | C12N 1/06 435/71.1 |
| 2011/0232161 | A1 | 9/2011 | Siskin et al. | |
| 2012/0005949 | A1 * | 1/2012 | Stevens et al. | 44/307 |
| 2012/0151827 | A1 * | 6/2012 | Powell et al. | 44/307 |
| 2014/0005422 | A1 * | 1/2014 | Kale | C11E 1/10 554/21 |
| 2014/0249338 | A1 * | 9/2014 | Roussis et al. | 585/24 |

FOREIGN PATENT DOCUMENTS

WO    2010-046115    4/2010

OTHER PUBLICATIONS

Zhang et al., Bioresource Technology, 2010; 101: 5297-5304.*
MadSciNetwork: Biochemistry, 2009, http://www.madsci.org/posts/archives/2009-12/1260943081.Bc.r.html.*
Chakraborty et al.; "Concomitant extraction of bio-oil and value added polysaccharides from Chlorella sorokiniana using a unique sequential hydrothermal extraction technology"; Fuel, vol. 95, 2012, pp. 63-70.

(Continued)

*Primary Examiner* — Gary Nickol
*Assistant Examiner* — Lakia Tongue
(74) *Attorney, Agent, or Firm* — Whitham, Curtis & Cook, P.C.

(57) ABSTRACT

Methods of producing bio-fuel and other high-value products from oleaginous biomass (e.g. algae biomass) are provided. The two-step methods use a first step of subcritical water extraction of the biomass at low temperatures to produce polysaccharides and other high value products of interest, followed by, ii) hydrothermal liquefaction of remaining solid biomass at high temperatures to produce bio-oil.

18 Claims, 10 Drawing Sheets

(56) References Cited

OTHER PUBLICATIONS

Miao et al.; "Impact of reaction conditions on the simultaneous production of polysaccharides and bio-oil from heterotrophically grown Chlorella sorokiniana by a unique sequential hydrothermal liquefaction process"; Bioresource Technology, vol. 110, 2012, pp. 617-627.

Biller et al.; "Potential yields and properties of oil from the hydrothermal liquefaction of microalgae with different biochemical content"; Bioresource Technology, vol. 102, 2011, pp. 215-225.

* cited by examiner

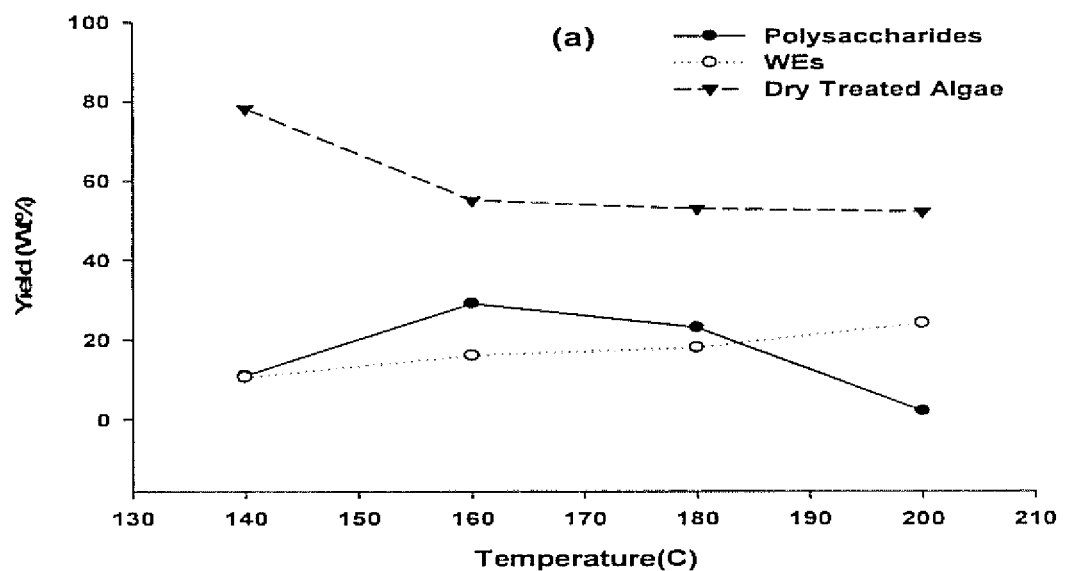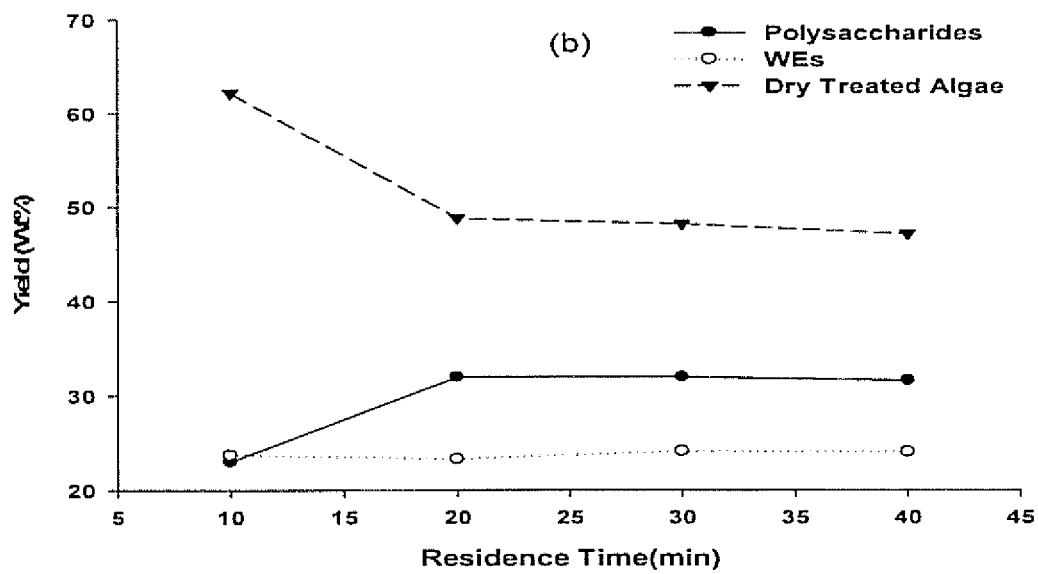
Figure 2A and B

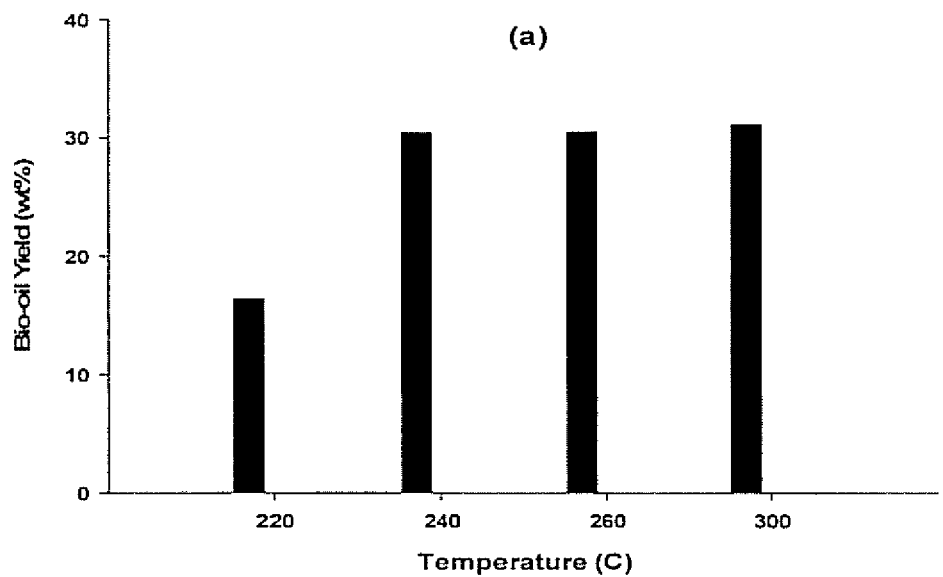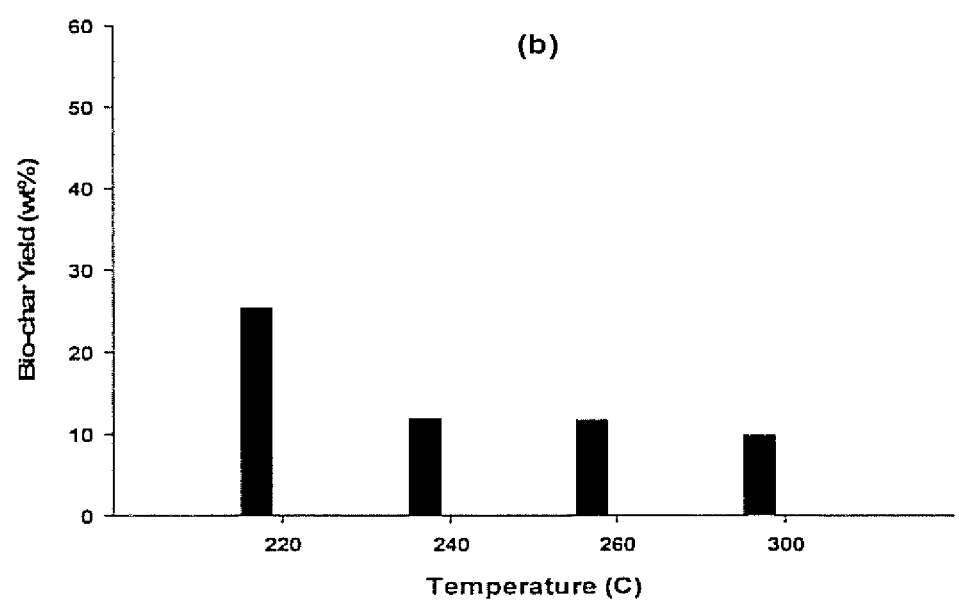
Figure 3A and B

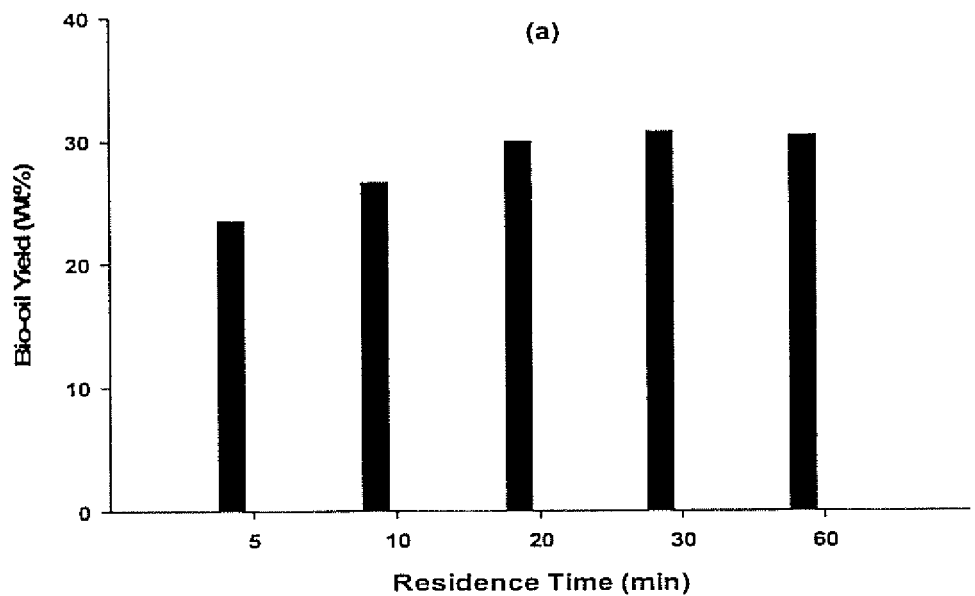
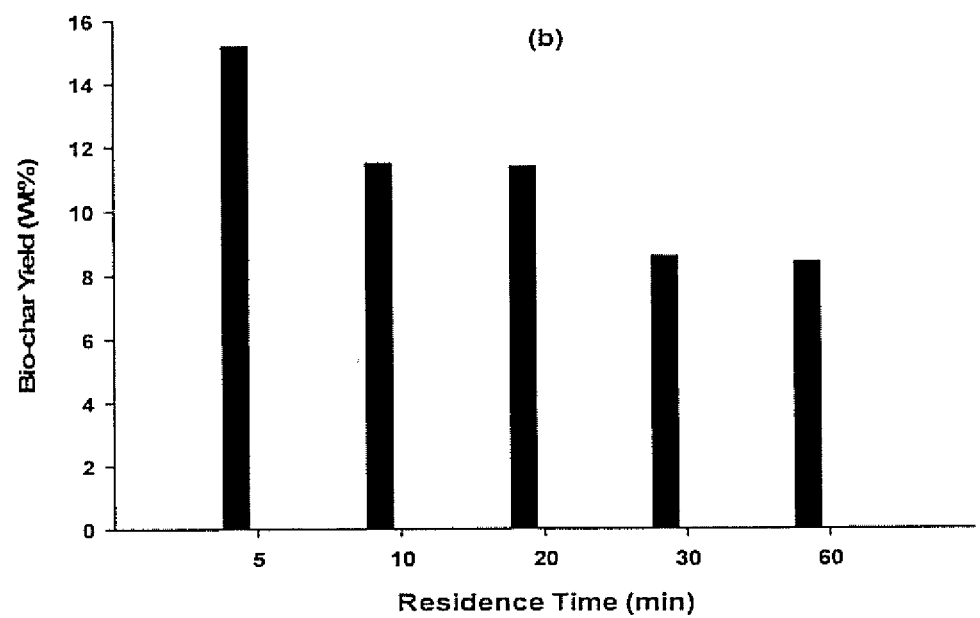
Figure 4A and B

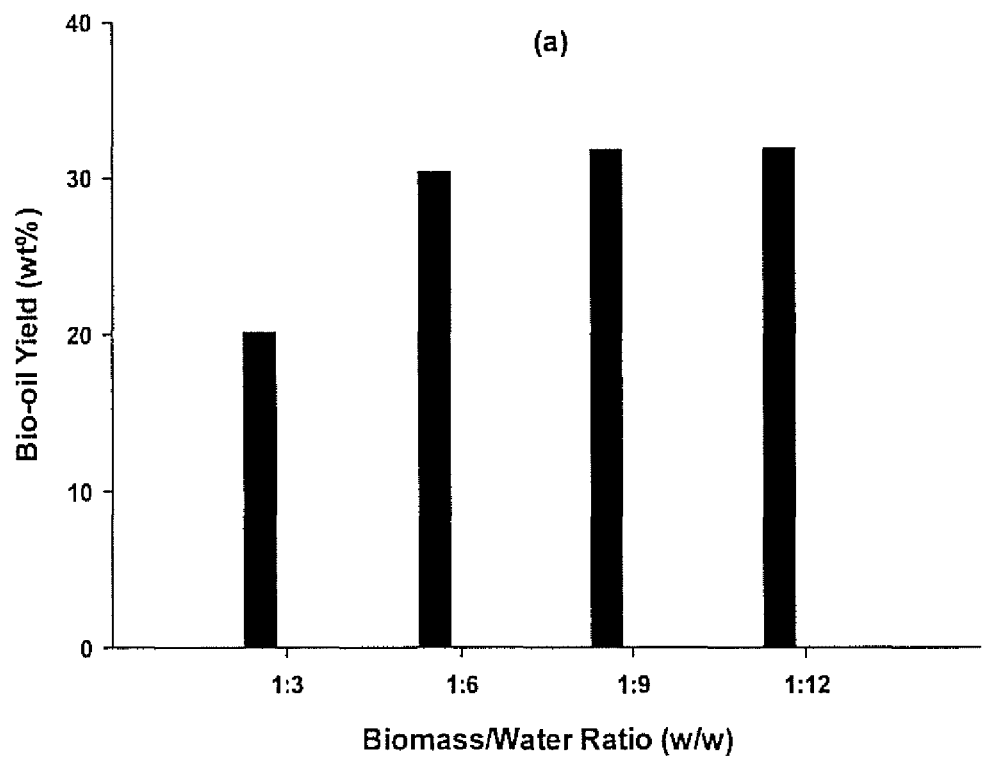
Figure 5A and B

SEQUENTIAL HYDROTHERMAL LIQUIFACTION (SEQHTL) FOR EXTRACTION OF SUPERIOR BIO-OIL AND OTHER ORGANIC COMPOUNDS FROM OLEAGINOUS BIOMASS

BACKGROUND OF THE INVENTION

1. Field of the Invention

The invention generally relates to improved methods of producing bio-fuel and other high-value products from oleaginous biomass such as algae. In particular, the invention provides two-step methods for the production of bio-oil and value-added compounds from algal-biomass using, in step 1, subcritical water extraction at low temperatures to recover co-products such as polysaccharides from a liquid phase; and using, in step 2, high temperature hydrothermal liquefaction of the remaining algae-biomass solids to produce bio-oils.

2. Background of the Invention

Algae as a potential feedstock for developing "drop-in" biofuel have attracted nationwide interest (e.g. development of the National Algae Road Map, the National Biofuel Action Plan, etc.). Unique characteristics of algae which set it apart from other biomass sources are 1) its high biomass yield per unit of light area 2) high oil content 3) oil content can be increased by tuning the culture conditions and 4) production does not require agricultural land, fresh water is not essential and nutrients can be supplied by waste water and $CO_2$.

However the main drawback in algal biofuel production is its cost of production. According to Van Harmelen and Oonk (2006) even with the most favorable assumptions about algal production costs, algal systems dedicated only to production of fuel are not economically feasible. Instead, the economic viability of biofuel depends largely upon the extraction of co-products.

Presently, co-extraction of value added compounds along with the bio-fuel is restricted due to technoeconomic barriers. The major bottleneck is the lack of efficient separation technology. Particularly troublesome is the fact that known methods of lipid extraction and algae biomass conversion (such as organic solvent extraction, hydrothermal liquefaction, and gasification) do not allow the separation of these compounds in their active forms.

Algae biomass is comprised of protein, carbohydrate and fatty acids. Unlike lignocelluloses, the major heating value of the bio-oil produced from the algae feedstock is contributed by the fatty acids. Specifically, if the starting biomass content has a moderate amount of fatty acids (26-30%), then in such a scenario the other two constituents of the biomass do not play a significant role in yield and high heating value of algae-based bio-oil, but rather complicate further processing of the bio-oil.

Hydrothermal treatment and solvent extraction are two processes capable of separating these chemicals in useable form. Solvent extraction has major disadvantages due to the cost and environmental impact of the solvents that are employed. In contrast, hydrothermal (HT) treatment offers a less problematic alternative. HT typically refers to near- and supercritical water systems held under anoxic (reducing) conditions. HT treatments of all types of biomass have resulted in transformation of the bio-molecules to mixtures of gas- and liquid-phase aromatic and aliphatic chemicals (Catallo et al., 2008). HT is attractive for processing algae because, unlike pyrolysis and solvent extraction, it can use wet algae biomass directly without requiring drying the feedstock. Depending on the targeted product states, HT typically involves gasification (HTG), liquefaction (HTL), and/or the use of both HTG and HTL. HTG generally takes place at higher temperatures (400-700° C.) (Peterson et al., 2008) and has the advantage of converting all types of organic molecules to simple gas mixtures such as methane or hydrogen; thus it is not sensitive to lipid content of the algae. However, the breakdown of bio-molecules which occurs as a result of the high temperatures limits the ability of HTG to produce various other high value co-products. HTL, taking place at 200-400° C., produces liquid products, often called bio-oil or bio-crude. HTL has been demonstrated to be effective for producing bio-oil using a range of micro-algae (Dote et al., 1993; Minowa et al., 1995; Yang et al., 2004). The main advantage of HTL is that it can be used to convert other non-lipid organic molecules also to fuel components; thus the total bio-oil yield is greater than the lipid content. For example, Dote et al., (1993) liquefied a strain of micro-algae that contained 50% natural oils at 300° C. with an $Na_2CO_3$ catalyst, and were able to produce a yield of 64% (mass basis) oil from this feedstock, showing that not only fat, but also other organics like protein, fiber, and carbohydrate are also converted into oil. However, Selhan Karagoz (2004) employed a low-temperature hydrothermal process to treat biomass (180° C., 250° C. and 280° C.) with reaction times of 15 min and 60 min, and found that during longer reaction times at 250° C. and 280° C., secondary reactions occurred and decreased the yield of oil products, with the majority of compounds in the oil containing less desirable $C_9$-$C_{11}$ carbons. Thus, a major disadvantage of HTL is that it results in production of a mixture of smaller carbon molecules, together with protein derivatives, resulting in production of bio-oils of lower quality than desired.

There are several studies which showed the channeling of carbohydrate components of biomass to bio-oil by using organic acid; however, and this procedure increases the total bio-oil yield by only about e.g. 3-4%. As mentioned in those reports, organic acids enhance the decarboxylation of the carbohydrate which further repolymerizes into complex structures which also form part of the bio-oil (Ross et al. 2010).

Compared to carbohydrate, protein in the biomass has higher thermo chemical bio-oil conversion efficiency. Ammonia produced via deamination of proteins acts both as a basic catalyst and a reactant, and shifts the sugar degradation mechanism from aqueous pyrolysis (which results predominantly in furan formation) to aldol and related condensation pathway (Nelson et al., 1984), leading to the production of more oily products. However, these chemical phenomena also introduce obnoxious nitrogenous compounds into the bio-oil. Removal of such nitrogenous compounds requires a complex and expensive denitrogenation process. Furthermore, in hydrothermal media under high temperature, carbohydrate/protein produces several toxic chemicals like furfural, hydroxymethyl furfural, nitrogenous aromatic compounds, etc. Due to the presence of such compounds, nutrient recovery and recycling of the aqueous phase becomes difficult. Hydrothermal pretreatment at lower temperature (at which solvolysis/hydrolysis are the dominant reactions) will remove carbohydrate/protein components prior to their conversion into such toxic chemicals. The removal of carbohydrate enhances the physical contact between water and lipid molecules, and increases the extraction efficiency (Libra et al., 2011).

There is thus a pressing need in the art to develop superior methods of producing high quality bio-oil and value added co-products.

SUMMARY OF THE INVENTION

The invention provides two-stage systems and methods for the controlled extraction of high-value co-products in the course of manufacturing bio-fuel from algae biomass. The systems and methods involve the sequential use of 1) sub-critical water extraction (SWE) followed by 2) hydrothermal liquefaction (HTL) of the extracted biomass. The combination of these processes into a single production scheme (referred to herein as SEQHTL) leads to the production of high quality bio-oils without compromising the quality of the associated high-value co-products.

It is an object of this invention to provide a process for obtaining polysaccharides from oleaginous biomass comprising 1) heating a mixture of oleaginous biomass and an aqueous medium to a temperature in the range of from 155 to 165° C.; 2) maintaining said mixture at said temperature for a period of time of from 15 to 25 minutes; then 3) recovering polysaccharides released from said oleaginous biomass from said mixture. In some embodiments, the step of recovering includes the steps of a) separating a liquid fraction of said mixture from a solid fraction of said mixture; and b) extracting polysaccharides from said liquid fraction. In some embodiments, the step of extracting is carried out via precipitation with ethanol. In some embodiments, the temperature is 160° C.; in some embodiments, the period of time is 20 minutes. The method may further comprise a step of recovering from said mixture co-products such as proteins, polypeptides, peptides and sugars. In some embodiments, the oleaginous biomass is algae biomass.

The invention also provides a process for obtaining bio-oils from oleaginous biomass comprising 1) heating a mixture of oleaginous biomass and an aqueous medium to a temperature in the range of from 237 to 243° C.; 2) maintaining said mixture at said temperature for a period of time of from 15 to 25 minutes; and recovering bio-oils produced during said step of maintaining. In some embodiments, the temperature is 240° C. In some embodiments, the period of time is 20 minutes. The step of recovering may be carried out via $CH_2Cl_2$ extraction of said mixture. In some embodiments, the oleaginous biomass is algae biomass.

The invention also provides a method for obtaining polysaccharides and bio-oils from oleaginous biomass, comprising i) heating an aqueous mixture comprising said oleaginous biomass to a first temperature in the range of from 155 to 165° C.; ii) maintaining said aqueous mixture comprising said oleaginous biomass at said first temperature for a first period of time of from 15 to 25 minutes; iii) separating a liquid fraction of said aqueous mixture comprising said oleaginous biomass from a solid fraction of said mixture; iv) recovering polysaccharides released from said oleaginous biomass from said liquid fraction, v) heating an aqueous mixture comprising said solid fraction to a second temperature in the range of from 237 to 243° C.; vi) maintaining said aqueous mixture comprising said solid fraction at said second temperature for a second period of time of from 15 to 25 minutes; and vii) recovering, from said aqueous mixture comprising said solid fraction, bio-oils produced during said steps of v) heating and vi) maintaining. In some embodiments, the step of iv) recovering polysaccharides is carried out by ethanol precipitation. In some embodiments, the first temperature is 160° C. and the second temperature is 240° C. In some embodiments, the first and second periods of time are 20 minutes. The method may further comprise a step of recovering from said liquid fraction a co-product selected from the group consisting of proteins, polypeptides, peptides and sugars. In some embodiments, the oleaginous biomass is algae biomass.

The invention further provides a system for bio-oil production, comprising: a first closed reactor configured to receive oleaginous biomass and heat said oleaginous biomass to a first temperature in the range of from 155 to 165° C. for a first period of time from 15 to 25 minutes, and a second closed reactor configured to receive reacted oleaginous biomass solids from said first closed reactor and heat said reacted oleaginous biomass solids to a second temperature in the range of from 257 to 263° C. for a second period of time from 15 to 25 minutes. In some embodiments, the first temperature is 160° C., the second temperature is 260° C., and the first and second periods of time are 20 minutes. The system may further comprise a computer operably connected to the system and programmed to cause the first and second closed reactors to carry out the methods of the invention. In some embodiments, the oleaginous biomass is algae biomass.

BRIEF DESCRIPTION OF THE DRAWINGS

FIG. 2A-C. Influence of reaction conditions on the first SEQHTL step products yields: (a) for reaction temperature; (b) for residence time; (c) for biomass/water ratio.

FIG. 3A-C. Influence of reaction temperature on the products yields of SEQHTL: (a) for bio-oil; (b) for bio-char; (c) for WEs.

FIG. 4A-C. Influence of reaction residence time on the products yields of SEQHTL (First step at 160° C.) and DHTL: (a) for bio-oil; (b) for bio-char; (c) for WE.

FIG. 5A-C. Influence of biomass/water ratio on the products yields of SEQHTL: (a) for bio-oil; (b) for bio-char; (e) for WEs.

DETAILED DESCRIPTION

Figure 1:
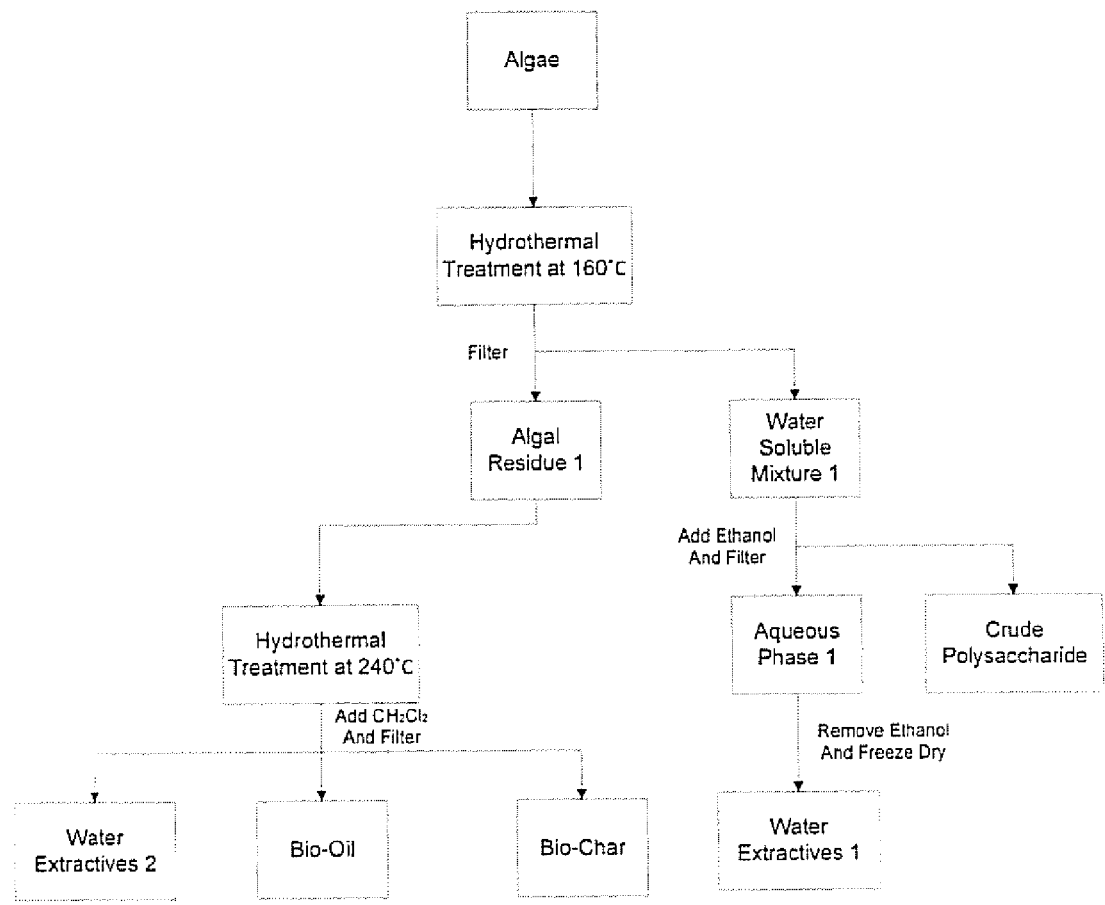
FIG. 1. Schematic diagram of the SEQHTL process.

The invention provides systems and methods involving hydrothermal pretreatment of algae biomass at low temperature followed by high temperature liquefaction to partially remove the carbohydrate and protein of the biomass which otherwise act as precursors for production of undesirable compounds in the bio-oil, thereby making the whole process economically viable. Further, the removed carbohydrate and protein components can be used to develop valuable co-products.

Removal of polysaccharides in the first step of the method contributes to economical algal bio-oil production as carbohydrates have a negative energy balance for their fairly low bio-oil yield and the enormous energy input required for conversion (Biller & Ross, 2011). Polysaccharides are reported to mainly contribute to the production of bio-char, which is of relatively low economic importance. In addition, the presence of carbohydrate in the final oil product makes recovery very difficult as the carbohydrate acts as an emulsifier and leads to the formation of bio-oil water emulsions which are difficult to separate. Therefore, removing significant amount of the carbohydrate prior to emulsification advantageously serves to decant the water without losing the oil phase. In contrast, in the practice of the present method, extraction of algal polysaccharides in their native form has large industrial potential in that a wide range of industrial products can be developed from algae polysaccharides.

Two-stage systems and methods are disclosed for the production of high quality biofuel (bio-oil). The systems and methods are designed to also optimize reaction conditions to produce high-value co-products by sequentially using the techniques of 1) sub-critical water extraction (SWE) of algal biomass followed by 2) hydrothermal liquefaction (HTL) of the extracted biomass. An exemplary representation of the process, referred to herein as "SEQHTL", is provided in FIG. 1. In some embodiments of the invention, the two steps are performed sequentially (in tandem, one after the other). In alternative embodiments, the two steps may be performed separately, e.g. step 1 may be performed alone for the purpose of producing products of interest such as polysaccharides, and step 2 may be performed alone for the purpose of generating bio-oil. Alternatively, steps 1 and 2 may be performed together, but only for the purpose of producing bio-oil, i.e. other co-products may or may not be recovered. In some embodiments, the media and various solvents utilized in the method can be captured or collected after use and recycled back into the system.

By "algal biomass" we mean a composition that generally comprises about 70% by dry-weight algae and about 30% by weight moisture. However, those of skill in the art will recognize that the ratios may vary somewhat, e.g. by about 5, 10, 15 or 20%.

The first phase of the high quality biofuel (bio-oil) production method described herein is subcritical water extraction (SWE) of algal biomass. SWE is based on the use of water, at temperatures just below the critical temperature, and pressure high enough to keep the water in a liquid state (Ayala and de Castro 2001). The "critical temperature" of a substance refers to the temperature at which it is between liquid and vapor phases, and above which a gas cannot be liquefied, regardless of the pressure applied. An underlying principal of SWE is that, under critical temperature at high pressure conditions, water becomes less polar and organic compounds are more soluble than at room temperature. Water as an extraction solvent at temperatures between 100 and 374° C. exhibits a unique characteristic. Under these conditions, the dielectric constant of water, i.e., its polarity, can easily and dramatically be lowered by increasing the temperature. Pure water at ambient temperature and pressure has a dielectric constant equal to 79, while increasing the temperature to 250° C. at a pressure of 5 MPa (necessary to maintain the liquid state) yields a significant reduction in dielectric constant to 27. This value is similar to that of ethanol at 25° C. and 0.1 MPa and, consequently, low enough to dissolve many compounds of intermediate or low polarity. Increasing the temperature at moderate pressure also reduces the surface tension and viscosity of water, which results in an enhanced solubility of compounds in this solvent. Using the methods described in this disclosure to control the dielectric constant of the water under conditions specifically designed to extract co-products from algae biofuel systems, a practitioner of the methods described herein can selectively extract different classes of compounds depending on the temperature used, with more polar compounds being typically extracted at lower temperatures and less polar compounds being extracted at higher temperatures. The selectivity of SWE thus allows for manipulation of the composition of the extracts by changing the operating parameters. For example, satisfactory recoveries (>90%) of polar compounds such as phenols are observed in water at temperatures below 100° C., and temperatures of about 200° C. are required for the quantitative extraction of less polar compounds. By utilizing this solvation property of water, this hydrothermal technology can be used as a tool for sequential extraction of value added products and bio-oil from algae biomass.

Accordingly, the first stage of the process involves exposing algal biomass to temperatures high enough to cause the breakdown of algal cell walls and release of biomolecules of interest (e.g. polysaccharides, proteins, etc.) into the surrounding medium, and yet low enough to prevent extensive degradation (e.g. hydrolysis) of the biomolecules.

Algal biomass is generally produced and harvested using known methods of cultivating algae, e.g. those described in e.g. U.S. Pat. No. 8,033,047 (Rasmussen, et al.); U.S. Pat. No. 8,017,377 (Much); U.S. Pat. No. 7,905,049 (Erd); and U.S. Pat. No. 8,211,307 (Chew, et al.), the complete contents of which are hereby incorporated by reference in entirety, including references cited therein. Those of skill in the art will recognize that many species and types of algae may be used in the practice of the invention. Exemplary algae which may be employed include but are not limited to: any *Chlorella* species, examples of which include but are not limited to *Chlorella vulgaris, Chlorella pyrenoidosa, Chlorella kessleri, Chlorella minutissima, Chlorella variabilis*, etc. Furthermore, any other oleaginous biomasses including, yeast and fungi, may also be employed.

Advantageously, since the first step of the method is carried out in an aqueous medium, it is not necessary to fully dry the algal biomass prior to the reaction. In some embodiments, the harvested algae may be dried or drained to remove excess water, and/or water or another suitable aqueous medium (e.g. saline, various buffered medias, etc. may be added to the harvested algae to achieve a biomass/water ratio in the range of from about 1:2 to about 1:20, or usually from about 1.3 to about 1:15, and more frequently from about 1:6 to about 1:12, e.g. about 1:6, 1:7, 1:8, 1:9, 1:10, 1:11 or 1:12. In some embodiments, the ratio that is used is about from about 1:7 to about 1:11 (e.g. about 1:7, 1:7.5, 1:8, 1:8.5, 1:9, 1:9.5, 1:10, 1:10.5, or 1:11). In some embodiments, the ratio that is used is about 1:9.

Also advantageously, it has been found that it is possible to keep the reaction temperatures sufficiently low to protect algal byproducts (e.g. polysaccharides, proteins, etc.) from extensive degradation and yet achieve high yields of the same. The first step of the method is thus generally carried out in a temperature range of from about 120 to about 220° C., e.g. at about 120, 125, 130, 135, 140, 145, 150, 155, 160, 165, 170, 175, 180, 185, 190, 195, 200, 205, 210, 215 or 220° C., at autogenous pressure, i.e. the saturated vapor pressure of the water and the partial vapor pressure of the biogases produced at that temperature under isothermal conditions. Those of skill in the art are familiar with methods of measuring and/or calculating vapor pressures, e.g. for water, the Clausius-Clapeyron relation or the Antoine equation may be used. In some embodiments, the reaction is carried out at temperatures between about 150 and 170° C., e.g. about 150, 155, 160, 165, or 170 for example, between about 155 to about 165° C. (e.g. about 155, 156, 157, 158, 159, 160, 161, 162, 163, 164 or 165° C.). In some embodiments, the temperature is 160° C.

The residence time in the reactor for the first step is typically in the range of from about 5 to 60 minutes, and usually from about 10 to 40 minutes, and even more frequently from about 15 to about 30 minutes, e.g. about 15, 20, 25 or 30 minutes (i.e. about 15, 16, 17, 18, 19, 20, 21, 22, 23, 24, 25, 26, 27, 28, 29 or 30 minutes). In some embodiments, the residence time is 20 minutes.

During the first step of the method, products of interest, which are generally water soluble biomolecules, are released from the algae that are treated. Exemplary products of interest include but are not limited to polysaccharides, proteins, polypeptides, peptides, sugars, etc. In some embodiments, the product of interest is one or more polysaccharides. In addition to polysaccharide the water extractive from step 1 is rich in amino acids, short peptides and sugars resulting from the partial hydrolysis of carbohydrates and protein which can be further processed, e.g. for nutrient recycling.

Those of skill in the art are familiar with methods of retrieving or separating (recovering) the various products of interest from the reaction mixture. For example, for polysaccharides the reaction mixture may be separated into liquid (generally aqueous) and solid fractions via e.g. filtration. The filtrate (indicated as Water Soluble Mixture 1 in FIG. 1) may then be treated with ethanol (e.g. 1:3 v/v ratio of ethanol to liquid fraction) to precipitate the polysaccharides, leaving behind an aqueous phase (Aqueous Phase 1 in FIG. 1). Optionally, the ethanol may be captured and recycled (reused). In other embodiments, any of the conventional starch separation technologies may be used, including but not limited to: reverse phase osmosis coupled with mechanical vapor recompression and/or ultra-filtration, etc.

The aqueous phase may be further processed to recover additional products (referred to in FIG. 1 as Water Extractives 1), for example, by various precipitation reactions, by affinity technologies (e.g. affinity chromatography, etc.). Prior to or in the course of these processes, the aqueous phase may be freeze dried, e.g. to facilitate handling, to concentrate a liquid phase, and/or to preserve products or materials of interest.

In some embodiments of the methods, step 1 may be repeated at a series of increasingly high temperatures in order to release particular types of molecules, or to release particular forms of molecules of interest, into the surrounding medium from which they can be recovered (e.g. isolated and/or purified) prior to increasing the temperature to the next highest level. In other words, step 1 may include a plurality of sub-steps carried out at different temperatures, prior to initiation of step 2.

In some embodiments of the invention, polysaccharides are advantageously recovered from step 1. For example, the physicochemical characterization (e.g. sugar composition analysis, linkage analysis and FTIR analysis) of *Chlorella sorokiniana* polysaccharide extracted by the SEQHTL method showed that the extracted polysaccharide is principally an α (1→4) linked glucan. Additionally, a comparison of its FTIR spectrum to that of a soluble potato starch showed that they resemble each other. Potential uses of the extracted α-glucan include but are not limited to: it can be hydrolyzed and used as a conventional feedstock, e.g. for bioethanol production, or as a sugar source for growing bio plastic-producing bacteria. Alternatively, it may be used for hydrogen production as well (Brányiková et al., 2011). Furthermore, it can be used in the production of thermoplastic starch (TPS), which is widely used, accounting for 50% of the bio plastic market (Inman, 2010). Typically, starch used for production of TPS must have more than 70% amylose content (Chaudhary, Torley, Halley, McCaffery & Chaudhary, 2009). Therefore, prior to the present invention, for TPS production from plant based starch, an energy expensive pre-processing (disbranching and removal of amylopectin) of the starch is required. In contrast, α-glucan isolated by the SEQHTL method advantageously does not require such processing.

Ultimately, after the water soluble products of interest are removed from the reaction mixture, the solid residue that is left (shown as algal residue 1 is FIG. 1) is further processed in the second step of the method. Prior to second step processing, the solid biomass residue may be separated e.g. by filtration, centrifugation, or some other separation method, and the solids are then re-suspended in water or a suitable aqueous medium. In the second step of the method, the total biomass is reduced to half, therefore water requirements in the second step are also reduced by half. This factors along with the development of extracted carbohydrate/protein as value added co-products, mitigates the cost of heating the water in steps 1 and 2 of the method. Alternatively, depending on the desired solid/liquid ratio, the solid solution may be used directly after removal of products of interest, e.g. by phase separation or other suitable technique. Typically, the second step is carried out using a biomass to water ratio in the range of from about 1:1 to about 1:14, and frequently from about 1:2 to about 1:13, e.g. about 1:2, 1:3, 1:4, 1:5, 1:6, 1:7, 1:8, 1:9, 1:10, 1:11, 1:12 or 1:13, In some embodiments, the ratio that is used is about from about 1:6 to about 1:12 (e.g. about 1:6, 1:6.5, 1:7, 1:7.5, 1:8, 1:8.5, 1:9, 1:9.5, 1:10, 1:10.5, 1:11, 1:11.5 or 1:12), and is generally in the range of from about 1:8 to about 1:10. In some embodiments, the ratio that is used is about 1:9.

The reaction temperatures for the second step are generally higher than those of the first step, e.g. in the range of from about 220 to about 300° C., e.g. about 220, 225, 230, 235, 240, 245, 250, 255, 260, 265, 270, 275, 280, 285, 290, 295, or 300° C. In some embodiments, the temperatures range from about 230 to about 250° C. (e.g. about 230, 231, 232, 233, 234, 235, 236, 237, 238, 239, 240, 241, 242, 243, 244, 245, 246, 247, 248, 249, or 250° C.).

The residence time in the reactor for the second step is typically in the range of from about 5 to 60 minutes, and usually from about 10 to 40 minutes, and even more frequently from about 15 to about 30 minutes, e.g. about 15, 20, 25 or 30 minutes (i.e. about 15, 16, 17, 18, 19, 20, 21, 22, 23, 24, 25, 26, 27, 28, 29 or 30 minutes). In some embodiments, the residence time is 20 minutes.

The second step of the method converts the residual biomass to bio-oils. The bio-oil thus processed is low in nitrogen content and rich in saturated fatty acid content. Separation (isolation, purification, substantial purification, extraction, etc.) of the oils is generally carried out using techniques that are known in the art, for example, those described in U.S. Pat. No. 8,217,211 (Agrawal, et al.). In some embodiments, $CH_2Cl_2$ is used to recover the bio-oils. After extraction, the oils may be treated or adapted as necessary for use as biofuel, e.g. as is, or after removal of nitrogen, or mixed with other fuels such as ethanol, various petroleum products, etc., as known to those of skill in the art.

Products left behind in the bio-oil recovery process include bio-char and water extractives, as shown in FIG. 1. By "bio-char" we mean the charcoal created by pyrolysis of biomass. Bio-char thus produced can be used, for example, as fertilizer and/or can be used as low-value fuel, etc. The water may be recycled for use in the methods.

In hydrothermal media under the temperatures used in step 2, carbohydrates and proteins can be converted to several toxic chemicals such as furfural, hydroxymethyl furfural, nitrogenous aromatic compounds, etc. Due to the presence of such compounds, nutrient recovery and recycling of the aqueous phase can be difficult. However, removal of carbohydrate and proteins at the lower temperatures employed in step 1 (at which solvolysis/hydrolysis are the dominant reactions) advantageously remove carbohydrate/protein components prior to their conversion into such toxic chemicals, making nutrient recovery more cost effective in the two-step methods described herein.

The invention also provides a system or apparatus for carrying out the methods described herein. The system is illustrated schematically in FIG. 6. As can be seen, the system comprises first reactor 10, in which step 1 of the method (sub-critical water extraction (SWE) is carried out. Suitable reactors are known to those of skill in the art, for example, batch bomb type reactors. First reactor 10 is capable of receiving (configured to receive) algal biomass for processing. First reactor 10 includes or is operably connected to heating mechanism 11, which may be adjustable, and is a closed reactor capable of retaining vapor generated during the heating required during step 1 of the method so that autogenous pressure builds up during the process, e.g. pressure equal to the saturated vapor pressure of the water in the reaction mixture. First reactor 10 is also configured with a means or mechanism to remove reacted algal biomass after the completion of step 1 in a manner that allows the reacted biomass to be separated into solid and liquid (water extractives) fractions. This may be accomplished in a variety of ways that are known to those of skill in the art, including an internal mechanism that actively pumps the liquid phase from the reactor, or a drain or straining mechanism that allows the liquid phase to leave the reactor, leaving behind the solid phase, etc. In addition, means of egress of the contents of first reactor 10 may be present, e.g. drains, pumps, channeling mechanisms, pipes, conduits, etc. Alternatively, the reacted biomass may be removed from the reactor and separation may be performed outside the reactor. In any case, if desired, the water extractives may be further processed to recover products of interest therein, as described herein, and the solids fraction from the reactor may be a) further processed according to step 2 of the method either in first reactor 10 (i.e. the liquid fraction is removed and the solid phase remains in the reactor; or 2) is transferred to second reactor 20 for further processing. In some embodiments, first reactor 10 and second reactor 20 may be operably connected to one another to facilitate transfer of the algae solids (which may be present in an aqueous medium) from first reactor 10 into second reactor 20, e.g. a pipe, conduit, conveyor belt, or other suitable transfer mechanism. Suitable media:algae solids mixtures may be formed 1) if optional second reactor 20 is not present, then after removal of a liquid phase from first reactor 10 but before heating first reactor 10 to temperatures required for step 2 of the method; or, if second reactor 20 is present 2) after removal from first reactor 10 but prior to transfer into second reactor 20; or after transfer into second reactor 20.

Second reactor 20 is also a closed reactor capable of retaining vapor generated during the heating required during step 2 of the method so that sufficient autogenous pressure builds up during the process, e.g. pressure equal to the saturated vapor pressure of the water in the reaction mixture (e.g. ~34 bar at 240° C.). Second reactor 20 also includes or is operably connected to heating mechanism 12, which may be adjustable. Second reactor 20 is capable of being heated to and maintaining the temperatures required to carry out step 1 of the method. Second reactor 20 is equipped with and/or operably connected to a means or mechanism for egress of bio-oils and water extractives therefrom, e.g. drains, pumps, channeling mechanisms, pipes, conduits, etc.

The system may also comprise one or more optional cooling apparatus 30, which may be attached to or included in one or both of the first and second reactors, or may be operably connected thereto. A single cooling apparatus 30 is depicted in FIG. 6, but a plurality may be present.

Figure 6:
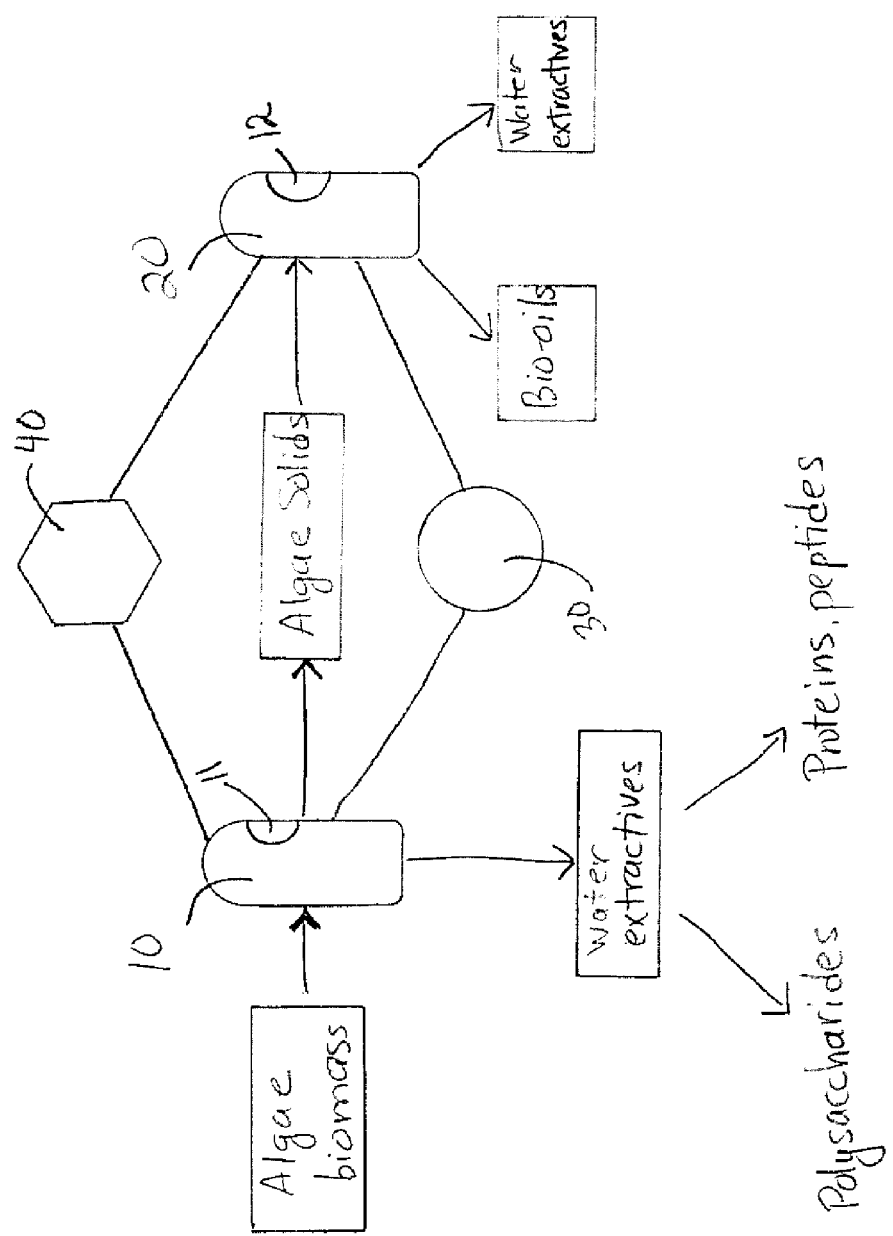
FIG. 6. Schematic representation of an SEQHTL system.

As illustrated in FIG. 6, the system of the method may be operably connected to and operable by a controlling element such as computer 40. The computer may programmed to cause the system to carry out the steps of the methods described herein e.g. to automatically open or close the reactor, attain the correct temperature for a suitable period of time, to cool the reactors, to monitor temperature and pressure, to monitor and correct fluctuations in reaction conditions, to automatically receive or eject the contents of the reactors e.g. by operating valves, etc. The computer may be operated locally and/or via the internet.

The following Examples section provides descriptions of exemplary embodiments of the invention but should not be construed as limiting in any way.

EXAMPLES

Example 1

A two-step sequential hydrothermal liquefaction (SEQHTL) method has been developed in which polysaccharide is extracted at the first step followed by bio-oil production in the second step. As described below, the effects of reaction temperature, residence time, and biomass/water ratio on the product distribution of each SEQHTL step have been evaluated. For step 1, the maximum yield of polysaccharides (32 wt %) was obtained by treatment of algal biomass at a temperature of 160° C. for 20 min with a 1:9 biomass/water ratio. For bio-oil extraction in step 2, when operation costs and bio-oil yield were taken into account, optimum results (>30% yield of bio-oil) were achieved by treatment of the residual algal biomass from step 1 at 240° C. for 20 min at a 1:9 biomass/water ratio.

Experimental Procedures

Raw Materials

The green alga *Chlorella sorokiniana* (UTEX 1602) was obtained from the Culture Collection of Alga at the University of Texas (Austin, Tex., USA). Heterotrophic stock culture was maintained at 30° C. in Kuhl medium supplemented with 10 g/l glucose. All media were autoclaved at 121° C. for 20 min before use.

Algal Biomass Preparation

The inocula was prepared in 500 ml flasks containing 200 ml Kuhl medium supplemented with 20 WI glucose, then fermentation of heterotrophic *Chlorella sorokiniana* was performed in a 5 L bioreactor with modified Kuhl medium supplemented with 40 g/l glucose and 2 g/l $KNO_3$ at 30° C. After 10 days cultured algae were harvested and centrifuged at 20° C. and 5000 rpm for 5 min. The algal paste was collected and 10 g of algae paste was placed into a 120° C. oven for 12 h in order to dry it and measure paste moisture.

Reaction Conditions and Protocols

Reactions were performed in a batch bomb type reactor (1 L, Parr4522, USA) with a heating rate of 5° C./min.

Direct hydrothermal liquefaction (DHTL) experiments, conducted for the purpose of comparison to the SEQHTL of the invention, were performed for a range of reaction temperatures (220° C., 240° C., 260° C., 300° C.), residence times (5 min, 10 min, 20 min, 30 min, 60 min), and biomass/water ratios (1:3, 1:6, 1:9, 1:12).

For SEQHTL experiments, 10 g dry weight harvested algal paste and distilled water were mixed thoroughly and introduced into the reactor. Nitrogen was bubbled for 5 min to purge oxygen from the system. In the first step, the runs were performed for a range of reaction temperatures (140°

C., 160° C., 180° C., 200° C.), residence times (10 min, 20 min, 30 min, 40 min), and biomass/water ratios (1:6, 1:9, 1:12). After finishing the first step of the reaction, the reaction mixture was collected and filtered with 90 µm filter paper. The filtrate was mixed with ethanol at a 1:4 ratio (water/ethanol, v/v) in order to precipitate the polysaccharides. The water mixture was subsequently centrifuged and the pellet of crude polysaccharides was air dried for 36 h and then weighed.

The residual algae that had been treated to remove polysaccharides ("treated algae", "TA") were returned to the reactor for the next step of liquefaction. To maintain the biomass/water ratio for the second step of SEQHTL-bio-oil extraction, the moisture content of the filtered TA was measured and water was added as necessary, prior to returning the mixture to the reactor for bio-oil extraction. In the second step runs were conducted under a range of temperatures (220-320° C.), residence times (5-60 min), and biomass/water ratios (1:3-1:12). After the final step, solids were found attached to the cooling pipe wall of the reactor. Reaction mixture was taken into the separating funnel and extracted with 50 ml of $CH_2Cl_2$. To remove all the oily products from the reaction mixture extraction was repeated for three times. The methylene chloride soluble fraction, which was defined as bio-oil, was measured following filtration and evaporation of $CH_2Cl_2$. The aqueous phase was filtered into two parts with a 90 µm filter paper: the solid residue was defined as bio-char was weighed after a 12 h dewatering in a 120° C. oven. The water soluble phase, defined as water extractives (WEs), was measured following a freeze drying, Product Yield The products of SEQHTL were bio-oil, polysaccharides, water extractives (WEs), and bio-char, while products from DHTL included bio-oil, bio-char, and WEs. The yields of each product were calculated on a dry algae mass basis and were calculated as follows:

$$\text{Bio-oil (wt \%)} = \frac{M_{bio\text{-}oil}}{M_{dry\ algae}} \times 100\%$$

$$\text{Polysaccharides (wt \%)} = \frac{M_{Polysaccharides}}{M_{dry\ algae}} \times 100\%$$

$$\text{WEs (wt \%)} = \frac{M_{WEs}}{M_{dry\ algae}} \times 100\%$$

$$\text{Bio-char (wt \%)} = \frac{M_{bio\text{-}char}}{M_{dry\ algae}} \times 100\%$$

where $M_{bio\text{-}oil}$ is the mass of bio-oil (g), $M_{dry\ algae}$ is the total mass of dry algae (g), $M_{polysaccharides}$ is the mass of polysaccharides (g), $M_{WEs}$ is the mass of WEs (g), and $M_{bio\text{-}char}$ is the mass of bio-char (g).

SEQHTL, Part 1: Polysaccharide Extraction Via Subcritical Water Extraction

Figure 2C:
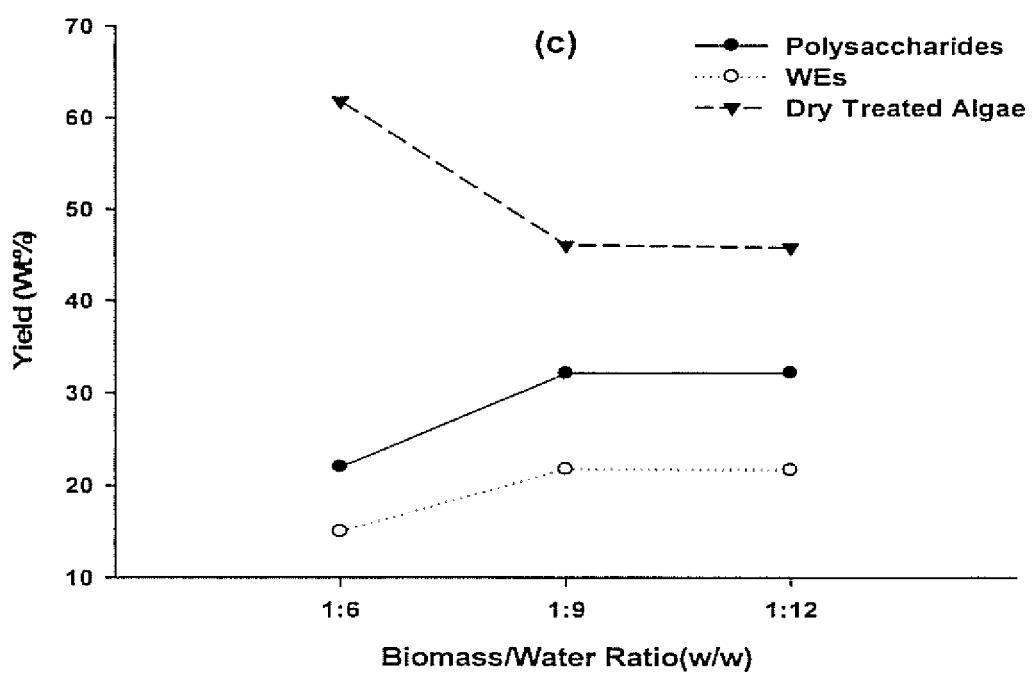

Target products of the first step of SEQHTL are polysaccharides. Therefore, an in-depth study was conducted to understand the impact of three reaction conditions; temperature, residence time and biomass/water ratio on the yield of polysaccharides. The results are shown in FIG. 2 A-C The first step of SEQHTL is designed to isolate polysaccharides in polymeric form, therefore criteria for selecting the temperature and residence time parameters focused on identifying optimal combinations of temperature, time and biomass/water ratio, which are sufficient to initiate hydrolysis of the complex, tensile algal cell wall yet capable of producing a high yield of polysaccharides in largely polymeric form. Various reaction temperatures (140° C., 160° C., 180° C., 200° C.) were studied at constant residence time of 20 min and a biomass/water ratio at 1:9. A maximum yield (29%) of ethanol insoluble polysaccharides was achieved at 160° C. The effective residence time to achieve the maximum yield of polysaccharides at a constant temperature of 160° C. with a biomass/water ratio of 1:9 was 20 min. Extending the time up to 40 min appeared to have no significant impact on the yield. The effect of biomass/water ratios from 1:6 to 1:12 on the yield of polysaccharides at 160° C. and 20 min residence time was also studied. A biomass/water ratio of 1:9 gave the highest polysaccharides yield; further increases in the amount of water did not result in a significant yield increase.

This data can be further explained from the yield of the dry treated algae residue (DTA). At 140° C. there is only a 22% decrease in the DTA from the original biomass (10 g), while at 160° C., a 45% decrease is observed. DTA amounts remain more or less constant at temperatures above 160° C. thus confirming that almost complete (substantially complete) release of the polysaccharides from the algal cell occurred at about 160° C. Therefore, at this particular biomass ratio, a 20 minute residence time at 160° C. is sufficient to hydrolyze the cell enough to release the polysaccharides into the hydrothermal media. However, this condition is not sufficient to completely hydrolyze the released polysaccharides into monosaccharides or small oligosaccharides. As a result, polysaccharides are obtained in their native or near-native (substantially native) form. As the temperature increases, polysaccharides begin to hydrolyze into sugars and the sugars then degrade further into small water soluble compounds which contribute to the yield of water extractives, consistent with the observation that the yield of water extractives is increased with increased temperatures, the maximum yield of water extractives (24%) being obtained at 200° C.

SEQHTL, Part 2: Bio-Oil Extraction Via Hydrothermal Liquefaction

Figure 3C:
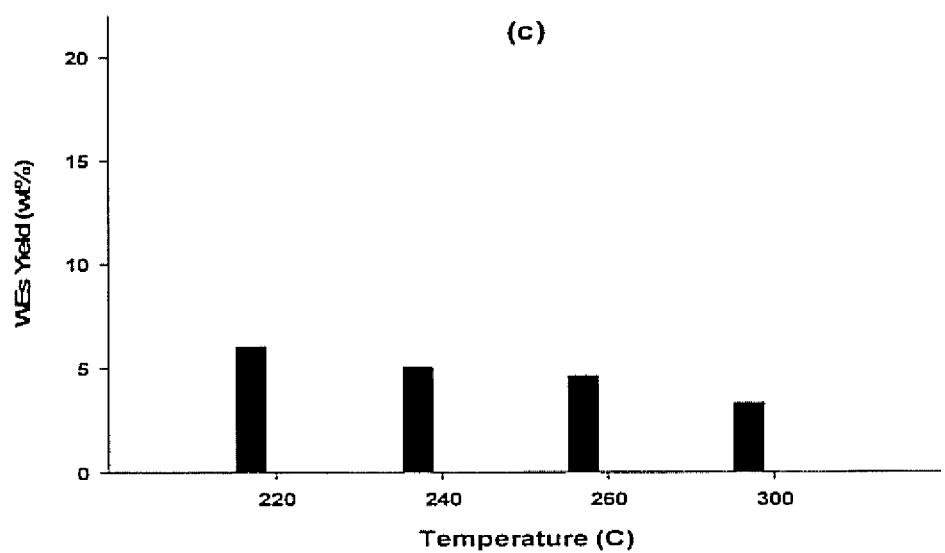

Dried treated algae residue that remained after polysaccharide extraction was subjected to further hydrothermal treatment in the second step of SEQHTL for bio-oil production. For each run, the previous first SWE step experimental conditions were kept constant at 160° C., 20 min with a biomass/water ratio at 1:9. The effect of reaction temperature on liquefied products distribution for SEQTHL was investigated in the temperature range between 220 and 300° C., with residence time of 1 hr, and biomass/water ratio at 1:9. Product yields are illustrated in FIGS. 3A-C. The values are reported on algae dry mass basis.

In case of SEQHTL maximum yield of bio-oil (~31%) was achieved at much lower temperature (240° C.). SEQHTL, yield of bio-oil improved sharply from 16.4 wt % at 220° C. to 30.4 wt % at 240° C. However, no significant increase in yield was observed when the temperature was increased beyond 240° C. Since the dielectric constant of water is negatively correlated to temperature, with increasing temperature water behaves more like an organic solvent and enhances the extraction of organic compounds from the biomass. Further, the ionic product of the water around 250° C. is much lower in comparison to water at room temperature. Thus, at high temperatures, water becomes a stronger acid and a stronger base, acting like an acid-base catalyst which also favors better extraction.

Treating the algal biomass at a much lower temperature (160° C.) in the first SEQHTL step makes the algal cell wall very fragile and porous. As a result during second step of SEQHTL much lower heat energy is required to disrupt the cell. The removal of carbohydrates in step 1 enhances the physical contacts between water and lipids molecules, and increases the extraction efficiency, since strong polysaccharide barriers prevent good contact between the solvent and cell components. In addition, the presence of excess polysaccharides during extraction is likely to form an emulsion, further impeding physical contacts and water diffusion, thereby reducing extraction efficiency. Thus, SEQHTL methods can attain higher yields at much lower temperatures.

Figure 4C:
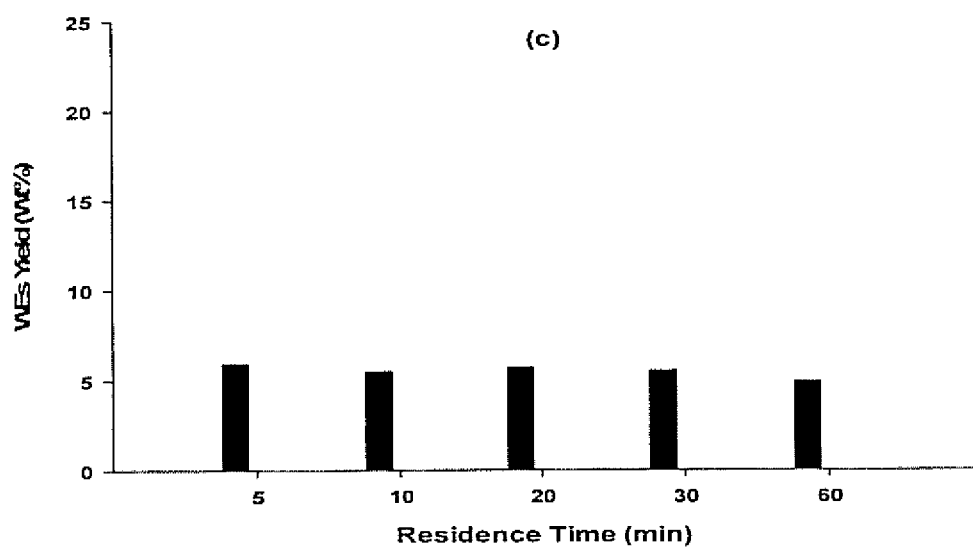

The reaction temperature of 240° C. and a biomass/water ratio of 1:9 were chosen to study the influence of residence time on bio-oil yield. Data presented in FIG. 4A-C illustrates that the highest conversion of algal biomass into bio-oil was achieved at a residence time of 20 min and 240° C. The results obtained demonstrated again that bio-oil yields increase with residence time and then reach a plateau at 20 min.

The effect on bio-oil yield of biomass/water ratios of 1:3, 1:6, 1:9, and 1:12 was investigated at constant conditions of 240° C. and 20 min residence time. It was observed that the biomass/water ratio had no significant impact on bio-oil yield at 240° C. (see FIG. 4A-C). However, biomass/water ratios below 1:9 reduced the bio-oil yield by 10%. Therefore, keeping industrial operations in mind, a biomass/water ratio of 1:9 was selected as optimal.

Figure 5C:
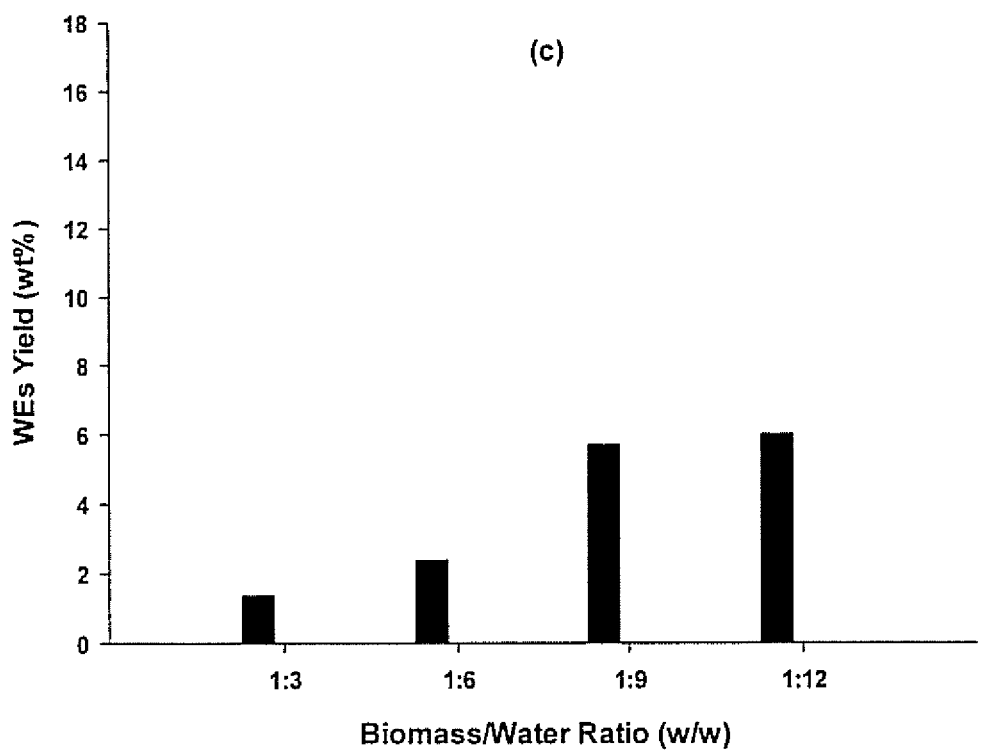

As is shown in FIG. 5A-C, removal of the polysaccharides prior to biomass liquefaction advantageously reduced the bio-char production by an average of 50%. Though the presence of bio char does not affect the bio-oil stability, its removal is essential as char causes difficulties in further processing of the bio-oil, e.g. hydrophobic components in the bio-oil may agglomerate with the char. This is more severe in case of algae bio-oil because the major components of the algae bio-oil are triglycerides and free fatty acids and these hydrophobic components attach to the surface of the bio char, requiring a harsh organic solvent extraction. In addition, char particles can also act as catalysts or nucleation sites to promote polymerization reactions between various bio-oil functionalities. Char can be removed by microfiltration; however, microfiltration can also remove valuable hydrocarbons, and thus by itself is not a necessary solution. Thus reduction of char formation that occurs due to the practice of the present methods (e.g. during the first step of SEQHTL) thus simplifies further storage and upgrading of the bio-oil.

Example 2

The elemental composition of the bio-oil extracted from the algae with solvents and the bio-oils obtained by DHTL (hydrothermal liquefaction conducted directly at 240° C.) and SEQHTL are presented in Table 1.

TABLE 1

Elemental analysis of carbon, oxygen, nitrogen, hydrogen, and sulfur; of crude algae bio-oil produced by SEQHTL and DHTL

| Products | C % | O % | N % | S % | H % | HHV (MJ/Kg) |
|---|---|---|---|---|---|---|
| Crude Algae | 50.4 | 37.4 | 2.91 | 0.21 | 7.9 | 21.63 |
| SEQHTL | 72.9 | 13.9 | 0.96 | 0.16 | 10.96 | 37.78 |
| DHTL | 73.8 | 14.97 | 1.35 | 0.14 | 10.31 | 36.97 |

The carbon contents in the bin-oils obtained by SEQHTL and DHTL were 72.9% and 73.8%, respectively. The oxygen content was less than 15% and Hydrogen contents were around 10% (see Table 1). This data shows that the nitrogen content in SEQHTL bio-oil is ~40% less than the DHTL bio-oil. Therefore, SEQHTL improves the quality of the bio-oil from the perspective of nitrogen. Nitrogen is undesirable due to NOx emissions during direct combustion and fouling of conventional oil-upgrading catalysts. Cyclic nitrogen compounds are particularly problematic during upgrading since they require ring hydrogenation to weaken the C—N bond before cleavage. Additionally, their high basicity can lead to adhesion to acidic active catalyst sites preventing further hydrotreatment reactions. The presence of the complex cyclic compounds also results in an increase in the molecular weight of the bio-oil. Therefore, bio-oil needs to be denitrified before it can be upgraded. Denitrogenation is an expensive process. Removal of nitrogen by the SEQHTL process prior to the bio-oil formation reduces or prevents the inclusion of nitrogenous compounds in the bio-oil and reduces the cost of denitrogenation.

The SEQHTL and DHTL bio-oil were further characterized to quantify the content of free fatty acids. The results are shown in Table 2.

TABLE 2

Comparative fatty acid analysis of the bio-oil produced by SEQHTL and DHTL

| Fatty Acid | Structure | SEQHTL$^a$ (mg/g) | DHTL$^b$ (mg/g) |
|---|---|---|---|
| Palmitic | C16:0 | 192.7 | 191.71 |
| Hexadecenoic | C16:1n9 | 41.37 | 33.5 |
| Stearic | C18:0 | 20.24 | 19.77 |
| Oleic | C18:1n9 | 200.97 | 136.97 |
| Octadecadienoic | C18:2n9 | 20.02 | 16.59 |
| Linoleic | C18:2n6 | 101.81 | 65.61 |
| Subtotal | | 577.11 | 464.15 |
| Others | | 126.95 | 208.64 |
| Total | | 704.06 | 672.79 |

$^a$mg/g of bio-oil produced by SEQHTL
$^b$mg/g of bio-oil produced by DHTL

The major six fatty acids obtained by Fatty acid methyl esters (FAMEs) analysis account for approximately 57.7% and 46.4% of the bio-oil by SEQHTL and DHTL, individually (Table 2). Thus, the bio-oil produced by SEQHTL is better in quality than the DHTL bio-oil in two ways one, less nitrogenous components and secondly, higher fatty acid content All references cited herein, including patents, patent applications and other publications, are hereby incorporated by reference in entirety.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Biller, P., Ross, A. B. 2011. Potential yields and properties of oil from the hydrothermal liquefaction of microalgae with different biochemical content. Bioresour. Technol. 102, 215-225.

Brányiková, I., Maršálková, B., Doucha, J., Brányik, T., Bišová, K., Zachleder, V., & Vítová, M. (2011). Microalgae-novel highly efficient starch producers. Biotechnology and bioengineering, 108(4), 766-776.

Chaudhary, A., Torley, P., Halley, P., McCaffery, N., & Chaudhary, D. (2009). Amylase content and chemical modification effects on thermoplastic starch from maize-Processing and characterisation using conventional polymer equipment. Carbohydrate Polymers, 78(4), 917-925.

Inman, H. (2010). Who said "potato"? Starch-based thermoplastics. Plastics engineering, 66(4), 42-44.

Karagoz S, Bhaskar T, Muto A, Sakata Y, Uddin M A. 2004. Low-temperature hydrothermal treatment of biomass: Effect of reaction parameters on products and boiling point distributions. Energy & Fuels 18(1):234-241.

Libra, J. A., Ro, K. S., Kammann, C., Funke, A., Berge, N. D., Neubauer, Y., Titirici, M.-M., Fühner, C., Bens, O., Kern, J., Emmerich, K.-H. 2011. Hydrothermal carbonization of biomass residuals: a comparative review of the chemistry, processes and applications of wet and dry pyrolysis. Biofuels 2, 71-106.

Minowa T, Yokoyama S, Kishimoto M, Okakura T. 1995. Oil Production from Algae Cells of Dunaliella-Tertiolecta by Direct Thermochemical Liquefaction. Fuel 74(12): 1735-1738.

Miranda M S, Sato S, Mancini-Filho J. 2001. Antioxidant activity of the microalgae *Chlorella vulgaris* cultured on special conditions. Boll Chim Farm 140(3):165-8.

Nelson, D. A., Molton, P. M., Russell, J. A., Hallen, R. T. 1984. Application of direct thermal liquefaction for the conversion of cellulosic biomass. Ind. Eng. Chem. Prod. Res. Dev. 23, 471-475.

Peterson A A, Vogel F, Lachance R P, Fr ling M, Antal M J, Tester J W. 2008. Thermochemical biofuel production in hydrothermal media: A review of sub- and supercritical water technologies. Energy & Environmental Science 1(1):32-65.

Ross, A. B., Biller, P., Kubacki, M. L., Li, H., Lea-Langton, A., Jones, J. M. 2010. Hydrothermal processing of microalgae using alkali and organic acids. Fuel 89, 2234-2243.

Yang Y F, Feng C P, Inamori Y, Maekawa T. 2004. Analysis of energy conversion characteristics in liquefaction of algae. Resources Conservation and Recycling 43(1):21-33.

We claim:

1. A process for obtaining polysaccharides from oleaginous biomass comprising heating a mixture consisting of oleaginous biomass and an aqueous medium to a temperature in the range of from 155 to 165° C.;

maintaining said mixture at said temperature for a period of time of from 15 to 25 minutes; then recovering polysaccharides released from said oleaginous biomass from said mixture.

2. The method of claim 1, wherein said step of recovering includes the steps of separating a liquid fraction of said mixture from a solid fraction of said mixture; and extracting polysaccharides from said liquid fraction.

3. The method of claim 2, wherein said step of extracting is carried out via precipitation with ethanol.

4. The method of claim 1, wherein said temperature is 160° C.

5. The method of claim 1, wherein said period of time is 20 minutes.

6. The method of claim 1, further comprising a step of recovering from said mixture a co-product selected from the group consisting of proteins, polypeptides, peptides and sugars.

7. The method of claim 1, wherein said oleaginous biomass is algae biomass.

8. A process for obtaining bio-oils from oleaginous biomass comprising separating a liquid fraction of an aqueous mixture comprising oleaginous biomass from a solid fraction of said aqueous mixture;

heating an aqueous mixture comprising said solid fraction of said mixture to a temperature in the range of from 237 to 243° C.;

maintaining said mixture at said temperature for a period of time of from 15 to 25 minutes; and recovering bio-oils produced during said step of maintaining.

9. The method of claim 8, wherein said temperature is 240° C.

10. The method of claim 8, wherein said period of time is 20 minutes.

11. The method of claim 8, wherein said step of recovering is carried out via $CH_2Cl_2$ extraction of said mixture.

12. The method of claim 8, wherein said oleaginous biomass is algae biomass.

13. A method for obtaining polysaccharides and bio-oils from oleaginous biomass, comprising i) heating an aqueous mixture comprising said oleaginous biomass to a first temperature in the range of from 155 to 165° C.;

ii) maintaining said aqueous mixture comprising said oleaginous biomass at said first temperature for a first period of time of from 15 to 25 minutes;

iii) separating a liquid fraction of said aqueous mixture comprising said oleaginous biomass from a solid fraction of said mixture;

iv) recovering polysaccharides released from said oleaginous biomass from said liquid fraction, v) heating an aqueous mixture comprising said solid fraction to a second temperature in the range of from 237 to 243° C.;

vi) maintaining said aqueous mixture comprising said solid fraction at said second temperature for a second period of time of from 15 to 25 minutes; and vii) recovering, from said aqueous mixture comprising said solid fraction, bio-oils produced during said steps of v) heating and vi) maintaining.

14. The method of claim 13, wherein said step of iv) recovering polysaccharides is carried out by ethanol precipitation.

15. The method of claim 13, wherein said first temperature is 160° C. and said second temperature is 240° C.

16. The method of claim 13, wherein said first and second periods of time are 20 minutes.

17. The method of claim 13, further comprising a step of recovering from said liquid fraction a co-product selected from the group consisting of proteins, polypeptides, peptides and sugars.

18. The method of claim 13, wherein said oleaginous biomass is algae biomass.

* * * * *

UNITED STATES PATENT AND TRADEMARK OFFICE
CERTIFICATE OF CORRECTION

PATENT NO. : 9,522,965 B2  
APPLICATION NO. : 14/353823  
DATED : December 20, 2016  
INVENTOR(S) : Shulin Chen et al.

It is certified that error appears in the above-identified patent and that said Letters Patent is hereby corrected as shown below:

In the Specification

Please insert the following paragraph in Column 1, beginning at Line 6:

--STATEMENT REGARDING FEDERALLY SPONSORED RESEARCH OR DEVELOPMENT
This invention was made with government support under grant number DE-EE0003112 awarded by the United States Department of Energy. The government has certain rights in this invention.--

Signed and Sealed this
Sixth Day of June, 2017

Michelle K. Lee
*Director of the United States Patent and Trademark Office*